(12) United States Patent
Cahill et al.

(10) Patent No.: US 6,406,602 B1
(45) Date of Patent: Jun. 18, 2002

(54) SAMPLE LOADING DEVICE FOR GEL ELECTROPHORESIS

(75) Inventors: Patrick B. Cahill; Jeffrey P. Montt, both of Natick, MA (US)

(73) Assignee: Genome Therapeutics Corporation, Waltham, MA (US)

(*) Notice: Subject to any disclaimer, the term of this patent is extended or adjusted under 35 U.S.C. 154(b) by 0 days.

(21) Appl. No.: 09/472,073

(22) Filed: Dec. 23, 1999

Related U.S. Application Data

(60) Provisional application No. 60/113,801, filed on Dec. 23, 1998.

(51) Int. Cl.[7] ............... G01N 27/26; C12M 1/26; B01L 3/02
(52) U.S. Cl. ............. 204/456; 204/466; 204/606; 204/619; 204/621; 435/309.1; 422/100
(58) Field of Search .............. 422/56, 57, 99, 422/100; 435/309.1, 309.3; 204/456, 464, 466, 606, 614, 619, 620

(56) References Cited

U.S. PATENT DOCUMENTS

| | | | |
|---|---|---|---|
| 4,079,739 A | * 3/1978 | Whitehead et al. | 604/365 |
| 4,629,563 A | * 12/1986 | Wrasidlo | 210/500.34 |
| 4,726,889 A | 2/1988 | Love et al. | 204/464 |
| 4,774,039 A | * 9/1988 | Wrasidlo | 264/41 |
| 4,889,606 A | 12/1989 | Dyson et al. | 204/464 |
| 4,960,691 A | * 10/1990 | Gordon et al. | 435/6 |
| 5,217,591 A | 6/1993 | Gombocz et al. | 204/466 |
| 5,318,682 A | 6/1994 | Singer | 204/466 |
| 5,405,516 A | 4/1995 | Bellon | 204/466 |
| 5,972,188 A | 10/1999 | Rice et al. | 204/456 |
| 5,980,709 A | * 11/1999 | Hodges et al. | 204/409 |

FOREIGN PATENT DOCUMENTS

| | | |
|---|---|---|
| WO | WO 96/27787 | 9/1996 |
| WO | WO 98/00706 | 1/1998 |

OTHER PUBLICATIONS

Erfle, H., et al., "Simultaneous loading of 200 sample lanes for DNA sequencing on vertical and horizontal, standard and ultrathin gels," Nucleic Acids Research, vol. 25, No. 11, 2229–2230 (Oxford University Press, 1997).

* cited by examiner

Primary Examiner—Jill Warden
Assistant Examiner—Alex Noguerola
(74) Attorney, Agent, or Firm—Hamilton, Brook, Smith & Reynolds, P.C.; Nina L. Pearlmutter, Esq.

(57) ABSTRACT

The present invention describes sample loading devices for use in polyacrylamide gel electrophoresis systems. The sample loading devices comprise alternating areas of absorbent membranes and diffusion barriers, where the diffusion barriers are formed by the application of some form of energy, such as heat, pressure, laser energy, RF energy or the like. The present invention also describes devices and methods for making sample loading devices, and methods of loading samples into polyacrylamide gel electrophoresis systems.

42 Claims, 8 Drawing Sheets

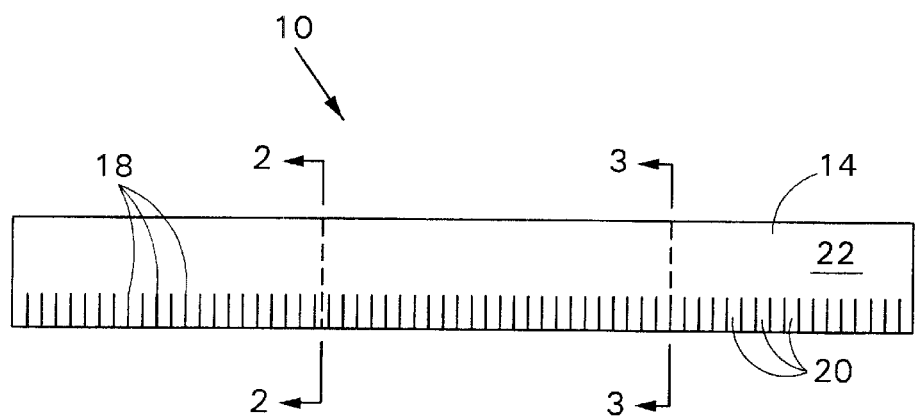
FIG. 1
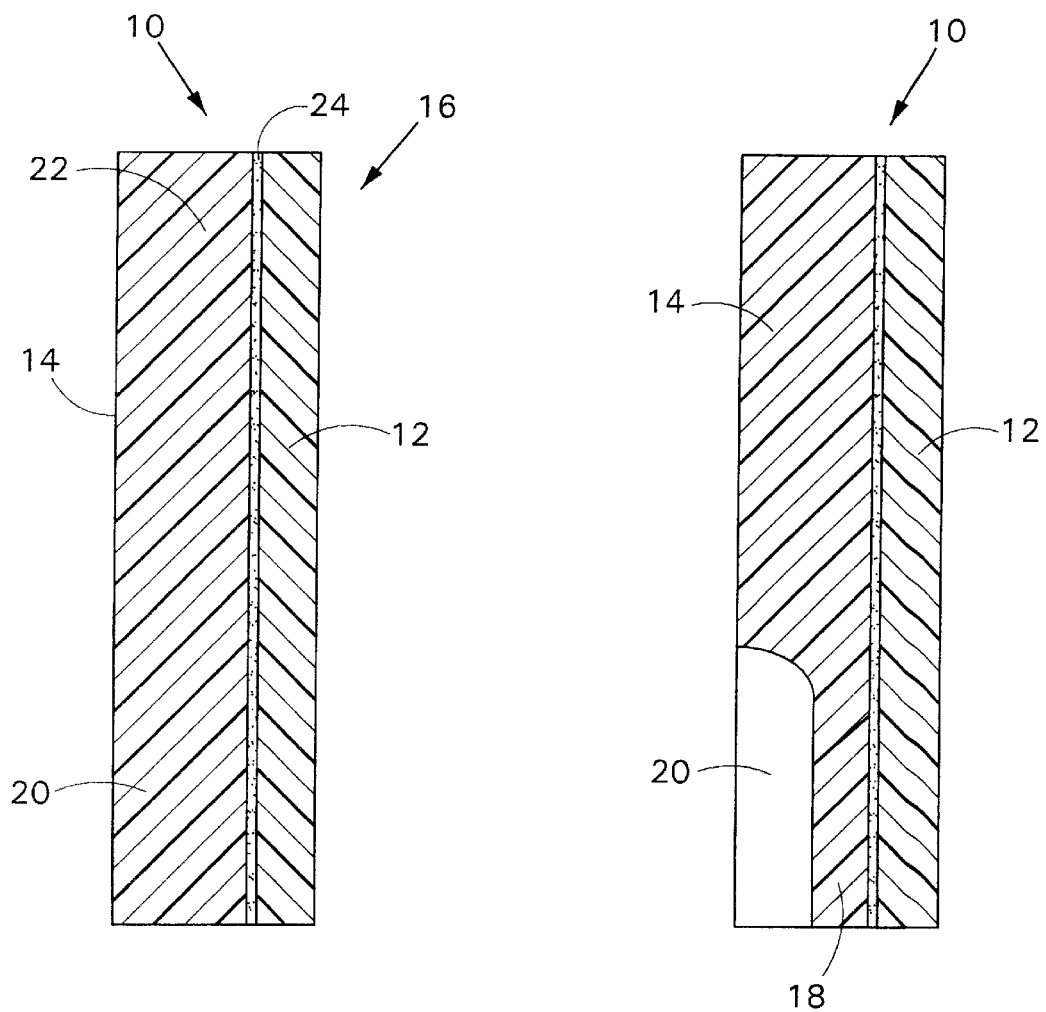
FIG. 2
FIG. 3

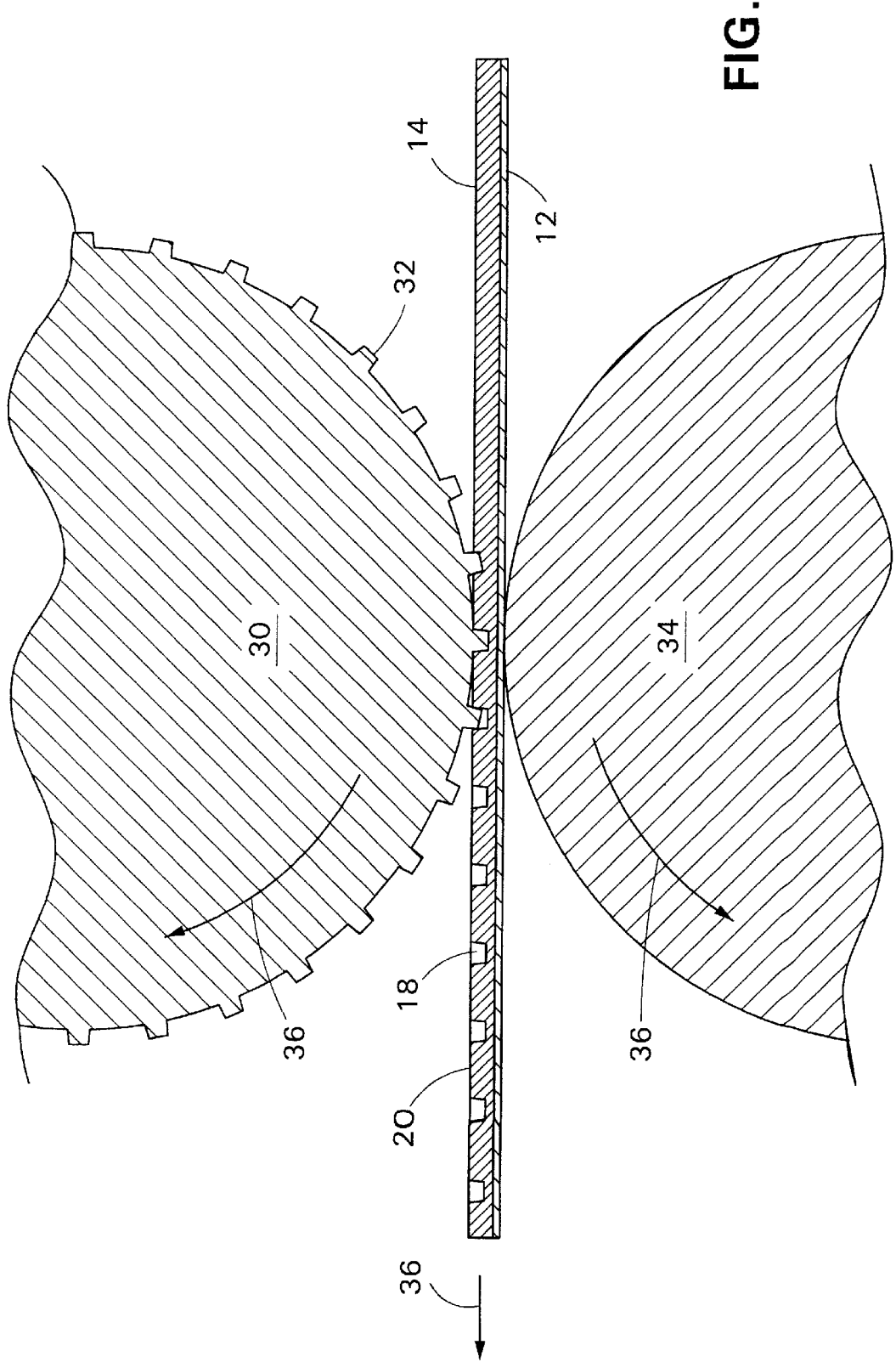

SAMPLE LOADING DEVICE FOR GEL ELECTROPHORESIS

RELATED APPLICATION

This application claims benefit to Provisional Application No. 60/113,801, filed Dec. 23, 1998, the entire teachings of which are incorporated herein by reference.

BACKGROUND OF THE INVENTION

Polyacrylamide gel electrophoresis is one of the most powerful tools used in the field of biotechnology. By passing an electric current through a polyacrylamide gel, the polyacrylamide gel electrophoresis method separates samples, such as nucleic acids, proteins and other biologically relevant molecules, by charge, size, conformation or other characteristics of the sample. One of the critical procedures in performing polyacrylamide gel electrophoresis is gel loading, which involves the addition of samples to the gel. To facilitate the sample loading process, many techniques and devices have been used. However, the loading process still remains one of the most time consuming and technique dependent steps in the polyacrylamide gel electrophoresis process.

One techniques involves using multiple syringes or pipettes to load the sample directly on the gel. Another technique is to use a sample loading device that has a substrate and an absorbent membrane on which a plurality of samples are loaded. A method of "diffusion isolation" is needed to prevent the individual samples from intermixing.

In the use of the substrate/absorbent membrane technique, it is known to use a sample loading device referred to as a "comb" that has a plurality of fingers that can help maintain the integrity of individual samples. For ensuring "diffusion isolation" of each sample within the loading area of the comb, the width of the absorbent material corresponding to the gel loading area is physically separated by cutting the comb into numerous "fingers." The length of the comb is constrained by the size of the gel and the corresponding "read" area of the apparatus which receives the comb, therefore the number of fingers and the physical separation between the samples is limited by this length of the comb. Furthermore, as the number of fingers and separating cuts is increased, the comb becomes less stable, making it more difficult to handle and place it into the gel.

Another embodiment of the sample loading device has scoring of the absorbent membrane (i.e., removing membrane material from the substrate) to produce barriers between the samples to maintain diffusion isolation. Another technique is creating diffusion isolation by use of hydrophobic ink on the absorbent material to produce barriers between the samples. The use of scoring or hydrophobic ink or a combination thereof is most effective when samples are resuspended in a water soluble solution; however, many loading buffers used for electrophoresis contain organic solvents that are unlikely to be impeded by a scored trough or by hydrophobic ink.

SUMMARY OF THE INVENTION

In the present invention, the properties of the absorbent membrane in a sample loading device are physically altered by pressure, heat, a combination of heat and pressure, or other such treatments, so that the regions between sample loading areas are unable to absorb the sample. The present method produces sample diffusion barriers that prevent sample diffusion and contamination with adjacent samples. The physical stability of the sample loading device is maintained because the membrane material remains continuous and lacks the unsupported "fingers" described in the prior art. Therefore, the present invention is more robust, making it easier to insert the sample loading device into a gel, thereby increasing data quality and resolution and reducing fabrication costs. Additionally due to the inherent and resultant properties of the absorbent and backing materials as a laminate, it is easier and more reliable to fabricate and apply standard quality and redundancy controls to the process/device than with prior art devices.

In one embodiment, the present invention describes a system that allows effective loading and scanning high resolution of about 48 or more samples in a standard polyacrylamide electrophoresis gel. The system produces results that are unexpectedly superior over prior art materials and methods. The sample loading device of the present invention also allows more samples to be loaded in a given area than other sample loading devices.

The sample diffusion barrier(s) of the present invention is formed utilizing the inherent properties of the absorbent membrane. The membrane is altered physically using pressure, conductive heat or convection heat (such as laser energy or RF energy), a combination of heat and pressure, or similar techniques. The material properties of the absorbent membrane are physically altered so that the absorbent membrane is changed into an effective, continuous diffusion barrier that is unable to absorb the sample. Thus, the sample loading device of the present invention with the homogenous altered absorbent membrane as the physical barrier between the sample loading areas, eliminates the need to add extraneous matter, such as hydrophobic inks, or to remove or prevent deposition of an absorbent material.

The present invention describes at least one sample loading device that comprises alternating areas of absorbent membranes and diffusion barriers. The diffusion barriers are formed by physically altering the absorbent membrane using heat, pressure, or combination pressure and heat, or other similar techniques.

At least one method of loading samples into a gel of an electrophoresis gel system is also described. The method includes applying a sample to a sample loading device, where the sample loading device comprises alternating absorbent and diffusion barrier areas of time membrane which areas are created by physically altering the absorbent membrane. The sample loading device is loaded onto the gel electrophoresis apparatus. A voltage is applied across the gel to establish an electrophoretic field which causes the sample to migrate into the gel and is subsequently scanned for analysis.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 is a side view of a sample loading device according to the invention;

FIG. 2 is a sectional view take along the line 2—2 of FIG. 1;

FIG. 3 is a sectional view taken along the line 3—3 of FIG. 1;

FIG. 5 is an enlarged view of part of the mechanism of FIG. 4;

DETAILED DESCRIPTION OF THE INVENTION

Figure 4:
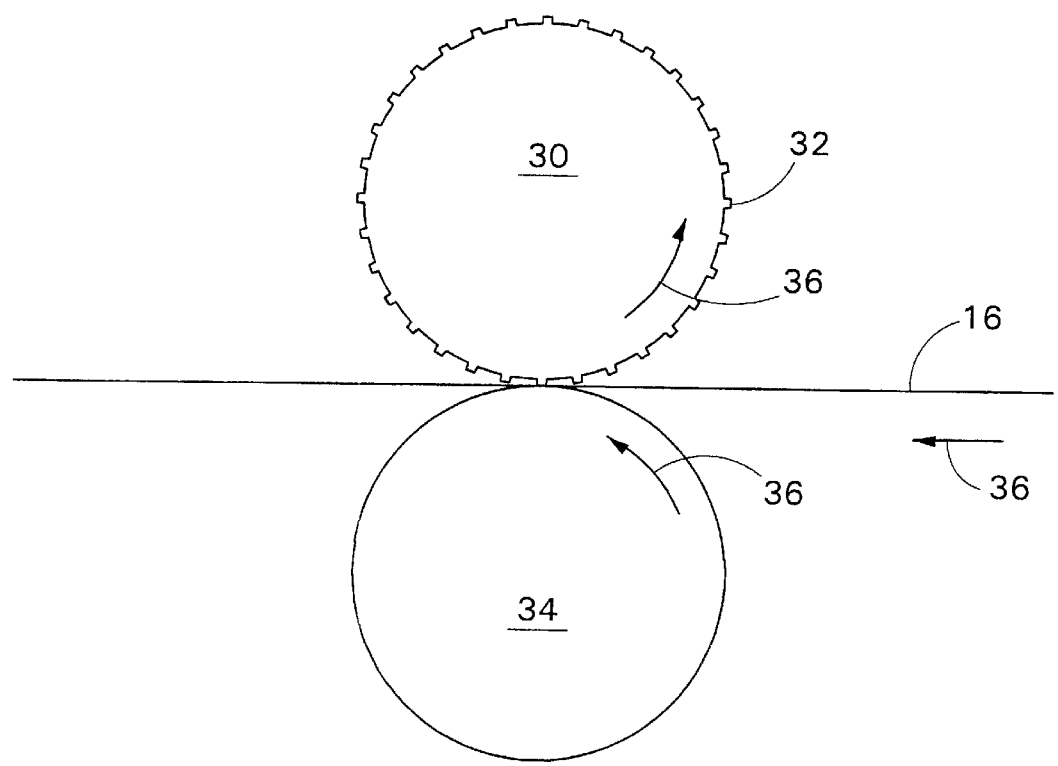
FIG. 4 illustrates rotary mechanism for producing a sample loading device of the present invention.

Referring to the drawings, where like numerals indicate like elements, there is illustrated in FIGS. 1–3 a sample loading device in accordance with the present invention, generally referred to as 10.

As seen in FIGS. 2 and 3, the sample loading device 10 for an electrophoresis gel is made of a backing material 12, that carries an absorbent membrane 14 to form a composite material (laminate) 16. In one embodiment, the backing material 12 has an adhesive 24 for securing the absorbent membrane 14 and the backing material 12 together.

This laminate 16 as further discussed below, utilizes the material properties of the absorbent membrane 14 and the backing material 12. The laminating of the absorbent membrane to the backing material is in contrast to the prior art casting-on of the absorbent to the substrate discussed above. The use of an unsupported absorbent, which can exist without a supporting book as required in the prior art, results in a more robust, adoptable sample loading device 10.

Referring to FIG. 1, the sample loading device 10 has a plurality of sample loading areas or lanes 20 separated from each other by interposed sample diffusion barriers 18. The diffusion barriers 18 are formed from the same absorbent membrane 14 as the sample loading areas 20, but the membrane is altered to reduce the absorbent property of the absorbent membrane 14 and create the barrier 18 as explained below. The upper portion of the sample loading device 10 has a non sample holding and labeling area 22, which use will be described in further detail below.

FIG. 2 is a cross sectional view of the sample loading device 10 taken along the line 2—2 of FIG. 1. This view shows the placement and orientation of the backing material 12 and absorbent membrane 14 relative to each other at one of the sample loading areas 20 and also shows the non sample area 22, which is used for handling and labeling.

FIG. 3 is a cross sectional view of the sample loading device 10 taken along the line 3—3 of FIG. 1. The diffusion barrier 18 is compressed/altered absorbent membrane 14 and is secured to the backing material 12. The compressed/ altered absorbent membrane 14 acts as a diffusion barrier 18 which is capable of inhibiting diffusion of the sample placed on the sample loading area 20 of the sample loading device 10. A sample loading area 20 is shown behind the diffusion barrier 18.

The sample loading device 10 shown in FIGS. 1–3 is representative of an embodiment of the invention and has a plurality of diffusion barriers 18 separating each of the sample loading areas 20. One such embodiment has a length of 7 inches and a height of 0.75 inches, with 64 sample loading areas 20. Each of the sample loading areas 20 has a width of 0.089 inches (2.25 mm). Each of the diffusion barriers 18 has a width of 0.035 inches (0.9 mm). The diffusion barrier 18 extends 0.028 inches (7 mm) upward from the bottom edge.

The backing material 12 is made of a non-reactive polymer film tape such as a polyamide film tape sold under the trademark Kapton™ tape or a polyester film tape sold under the tradename Mylar™ tape. Both tapes are manufactured by DuPont and sold by Furon/CHR of New Haven, Conn. In a preferred embodiment, the backing material is "Nelatp-581" by Dielectric Polymers, Inc., which is a stable (polyester-like) adhesive backed material preferably. The adhesive is an inert silicone pressure sensitive adhesive. The tape has a width of approximately 0.75–1.00 inches, a thickness (carrier plus adhesive) of between 0.0018 and 0.0026 inches (0.45 and 0.67).

The absorbent membrane in a preferred embodiment is any available, DNA transfer membrane, which is an unsupported, neutrally-charged nylon "Biodyne-A Xu/Xu" or Polysulphone absorbent material (Pall Specialty Materials, Port Washington, N.Y.). The absorbent material has a total average thickness of between 0.0100 and 0.0161 inches (0.254 and 0.410 mm) and a pore size of between 0.12 and 0.50 μm. The pore size in a preferred embodiment is reduced by at least 90 percent in the diffusion barriers.

The laminate 16, in a preferred embodiment, is produced by rolling or applying the backing material 12, which contains adhesive 24, onto the absorbent membrane 14. The resultant laminate 16, as an unformed sample loading device is then subjected to a process which selectively alters the inherent mechanical properties of the absorbent membrane. The process may use pressure, conductive heat, convective heat (such as Laser or RF energy) or a combination of pressure, and heat, or other similar technique to create the sample diffusion barriers 18, to produce the sample loading device 10 as explained below. The sample diffusion barriers 18 prevent samples from cross contamination and/or diffusion to the adjacent samples on the sample loading device 10.

In using mechanical pressure method to form diffusion barriers, the laminate 16 is directed to a forming roller 30 as seen in FIG. 4 that has been fabricated with a predetermined pattern of teeth-like raised areas 32, which are of such size and spacing to produce the proper size and spacing of the sample diffusion barriers 18 and sample loading areas 20. As the laminate 16 is fed to the roller 30, a platen 34 opposes the roller 30 to ensure that the absorbent material layer of the laminate 16 will be compressed against the platen 34 in areas corresponding to the teeth 32 of the roller 30 to form the sample diffusion barrier 18 as best seen in FIG. 5. The arrows 36 indicate the direction of motion of the roller 30, the platen 34, and the laminate 16. The platen 34 can either be stationary or rotary. In utilizing a stationary platen, the forming roller travels transversely, parallel to the solid (platen) surface 34. This process alters the material properties of the absorbent membrane 14 to create a pattern of sample diffusion barriers 18.

Figure 6:
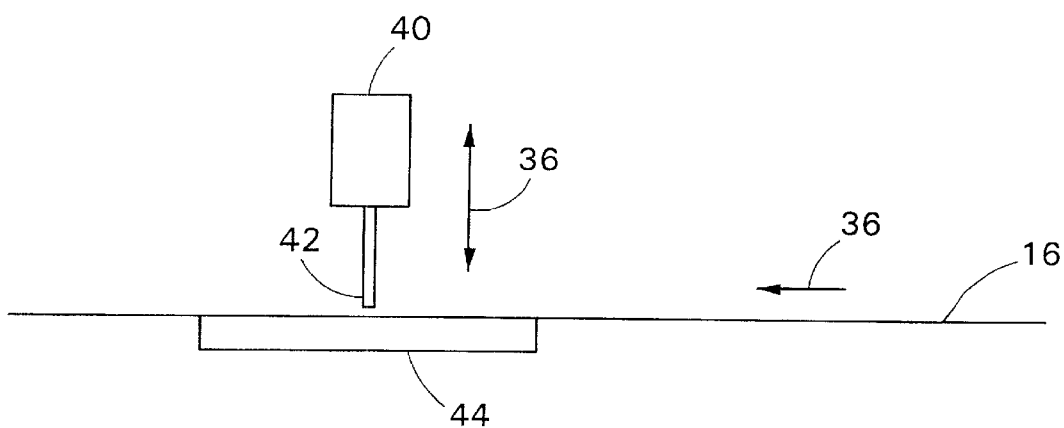
FIG. 6 illustrates linear mechanism for producing a sample loading device of the present invention.

An alternative to using rotary action to form diffusion barriers by utilizing mechanical pressure is to use a linear motion also utilizing mechanical pressure acting in a plane perpendicular to the laminate surface, as shown in FIG. 6. A stamping device 40 with at least one projection or edge 42, is attached to a mechanism which moves in a predetermined index linear motion. In one preferred embodiment, the edge 42 is near knife edge in shape and biased by a spring loaded mechanism (not shown). The stamping device 40 as seen in FIG. 6 employs a linear, vertical motion. A stationary platen 44 opposes the stamping device 40. The laminate 16 is subjected to the pressure between the stamping device 40 and platen 44, which alters the configuration and material properties of the absorbent membrane to create sample diffusion barriers. The arrows 36 indicate the direction of motion of the stamping device 40. The arrow 37 indicates the direction of the reciprocating motor of the platen 44. This operation can be either continuous or non-continuous, depending on the sequence of operations in processing the sample loading device. It is recognized that the laminate material can be fed into the forming device continuously thereby creating a quantity of formed laminate, which is then cut to the desired lengths for sample loading, or individual lengths of laminate material can be formed for sample loading and insertion into the gel electrophoresis apparatus.

Figure 7:
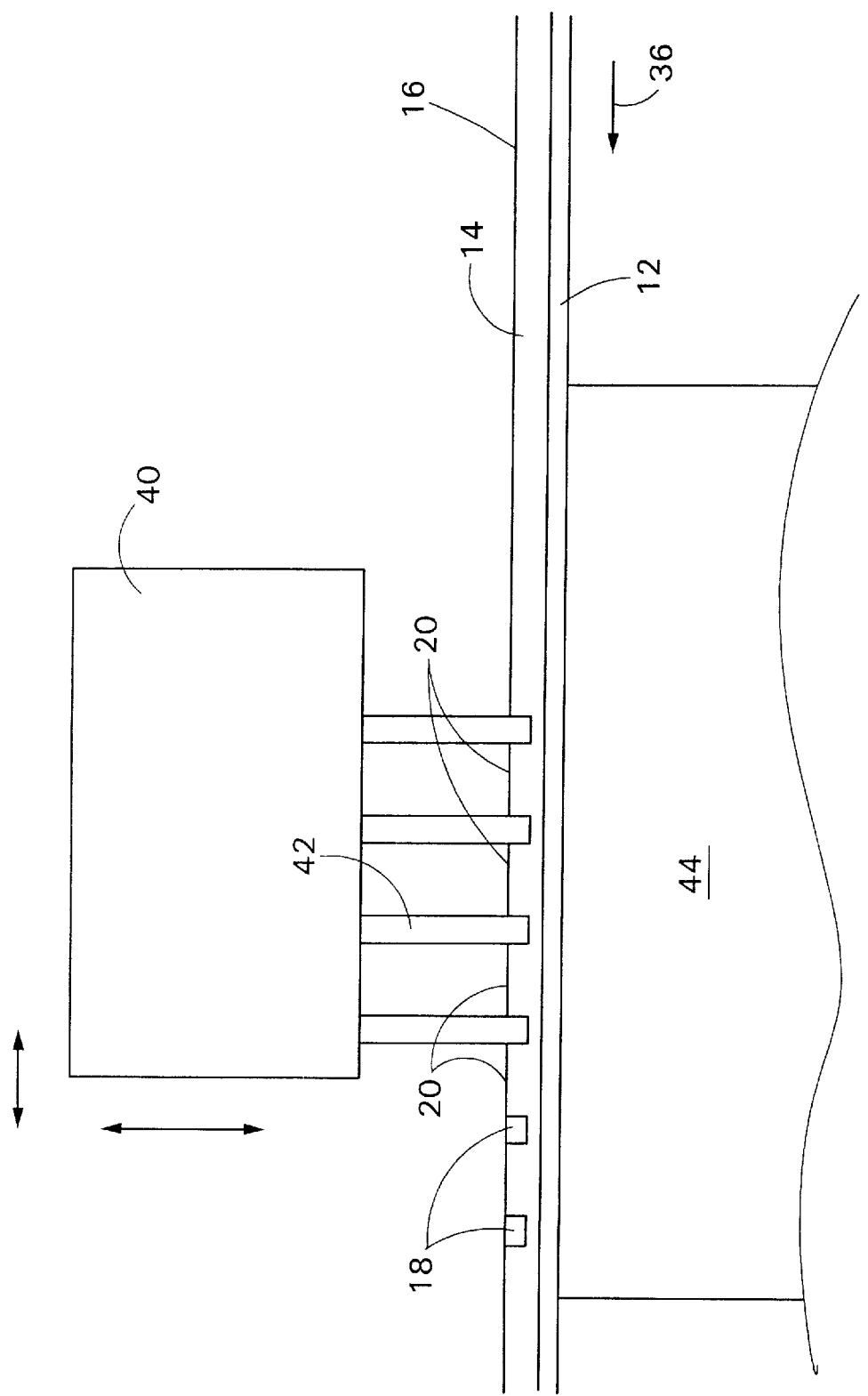
FIG. 7 shows an alternate linear mechanism for producing a sample loading device.

FIG. 7 shows an alternative embodiment of the stamping device 40 in which there are a plurality of projections 42 which are sized and spaced to produce the proper size and spacing of the sample diffusion barriers 18 and sample loading areas 20. The stamping device 40 can also produce a horizontal translation motion, in addition to having a vertical motion, to move the laminate 16 to the left as it creates the sample diffusion barriers 18. The stamping device 40 as it is raised moves to the right prior to engaging the laminate 16 again.

It is recognized that the stamping device 40 of FIG. 7 can move in a pure vertical direction with movement of the laminate 16 controlled by other mechanism. Likewise, the stamping device 40 of FIG. 6 likewise can additionally move in a horizontal direction. Other means of applying pressure to the laminate 16 can also be used. The amount of pressure applied to the absorbent membrane to create the diffusion barriers is preferably 2500 psi or greater, and can be in the range of 25,000 to 40,000 psi for a stamping device with 10 projections 42.

In addition to applying pressure, heat in combination with pressure can be used to create diffusion barriers 18. Less pressure is required to compress the membrane in this embodiment. For example, in one embodiment with the projections 42 heated to approximately 100° F. the amount of pressure needed to create the diffusion barriers can be reduced to 5000 psi for a stamping device with 64 projections 42.

Figure 8:
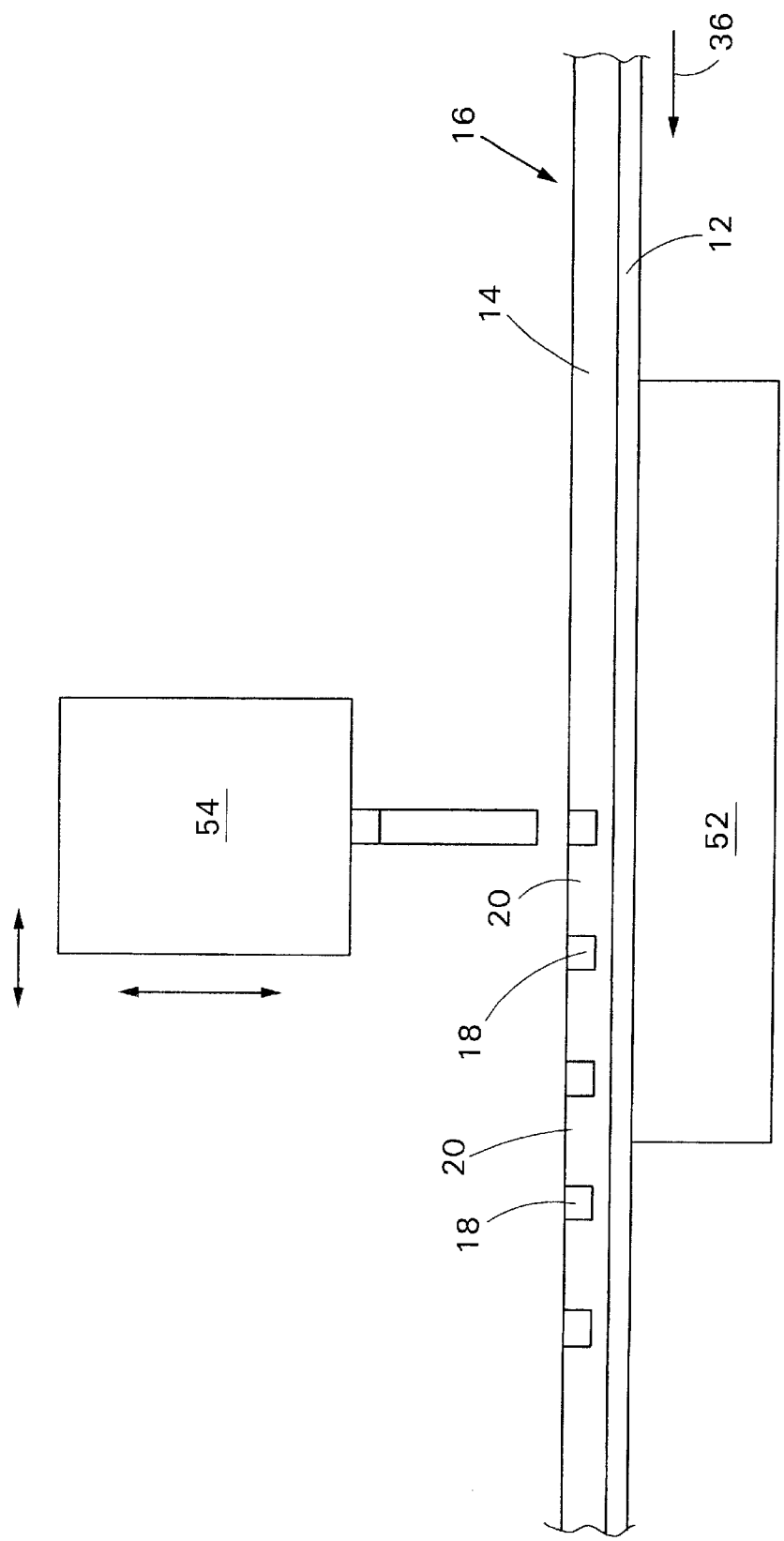
FIG. 8 is a schematic illustration of an RF energy producing mechanism to form a sample device.

An alternative method to using pressure, or the combination of heat and pressure to create the sample diffusion barrier 18 discussed above, is to apply heat, such as RF energy or laser energy, to the sample loading device to form the sample diffusion barriers 18. An example of this is illustrated in FIG. 8 When using laser energy or RF energy, the laminate 16 can be attached to or inset on, either temporarily or for the duration of the process, a carrier or surface 52 (also called a platform) that provides a stable and precise platform for the sample diffusion barrier 18 formation process. This platform 52 may be electrically and/or thermally insulating or electrically and/or thermally non-insulating. A laser, RF-generator or similar energy collating, amplifying or focusing device 54 can be positioned and guided so that when exposed to this energy, the material properties of the absorbent membrane 14 are altered to create a pattern of sample diffusion barriers 18. This operation can either be continuous or non-continuous, depending on the sequence of operations in processing the sample loading device. Other means of applying convection heat in the form of laser energy or RF energy to the absorbent material layer of the laminate can also be used as described above. The amount of laser energy or RF energy applied to the absorbent membrane layer of the laminate to create the diffusion barriers is preferably equivalent to the amount that creates a temperature sufficient to alter the material properties of the absorbent material.

Figure 9A:
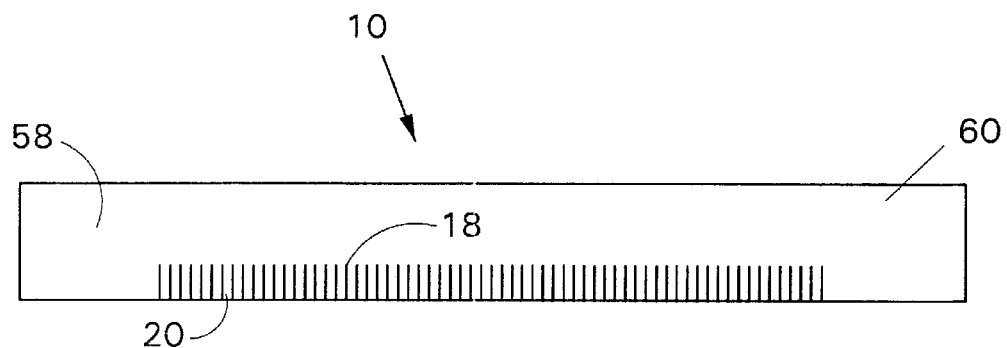
FIGS. 9A and 9B depict alternative embodiments of sample loading devices containing 64 and 96 sample loading areas, respectively.
Figure 9B:
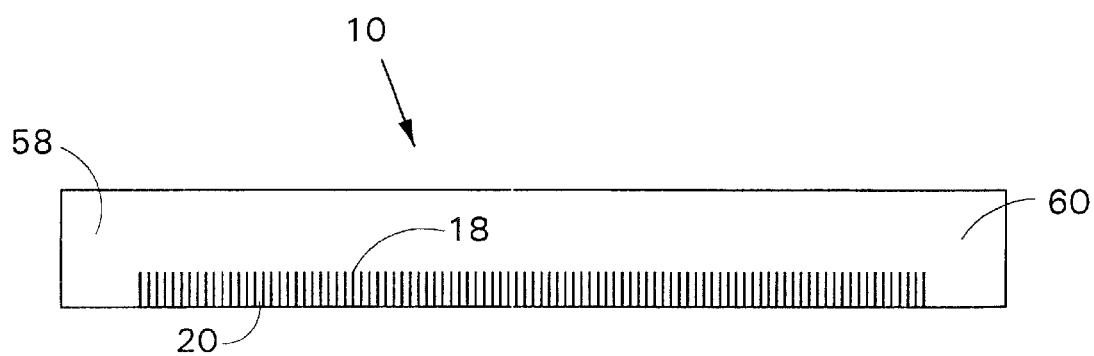

An alternate embodiment of the sample loading device 10 is shown in FIGS. 9A and 9B. These embodiments of a sample loading device 10 can be formed by the methods outlined above. The sample loading device 10 is made such that the sample loading areas 20 do not extend the length of the device 10. The sample loading device 10 can include a left margin 58 and a right margin 60 which can allow a user to grasp the sample loading device 10 from the side without the danger of disrupting samples placed on the sample loading areas. Additional alignment indicators or nomenclature can be located in these areas.

In one embodiment, the sample loading device 10 has 64 sample loading areas 20 as shown in FIG. 9A. One such example has a length of 7 inches and a height of 0.75 inches. Each of the sample loading areas 20 has a width of 0.089 inches (2.25 mm). Each of the diffusion barriers 18 has a width of 0.035 inches (90 mm). The diffusion barrier 18 extends 0.28 inches (70 mm) upward from the bottom edge.

The embodiment shown in FIG. 9B is a sample loading device 10 having 96 sample loading areas 20. One such example has a length of 7 inches and a height of 0.75 inches. Each of the sample loading areas 20 has a width of 0.089 inches (2.25 mm). Each of the diffusion barriers 18 has a width of 0.035 inches (0.90 mm). The diffusion barrier 18 extends 0.28 inches (7.0 mm) upward from the bottom edge.

After formation of the sample loading device 10, the samples can be added to the sample loading device 10 by, for example, manually spotting the samples with a hand pipette or by automatically spotting the samples, either one at a time or multiple devices, using a robotic workstation. The samples can be any samples known in the-art, including, for example, nucleic acids, proteins and other biologically relevant molecules.

Figure 10:
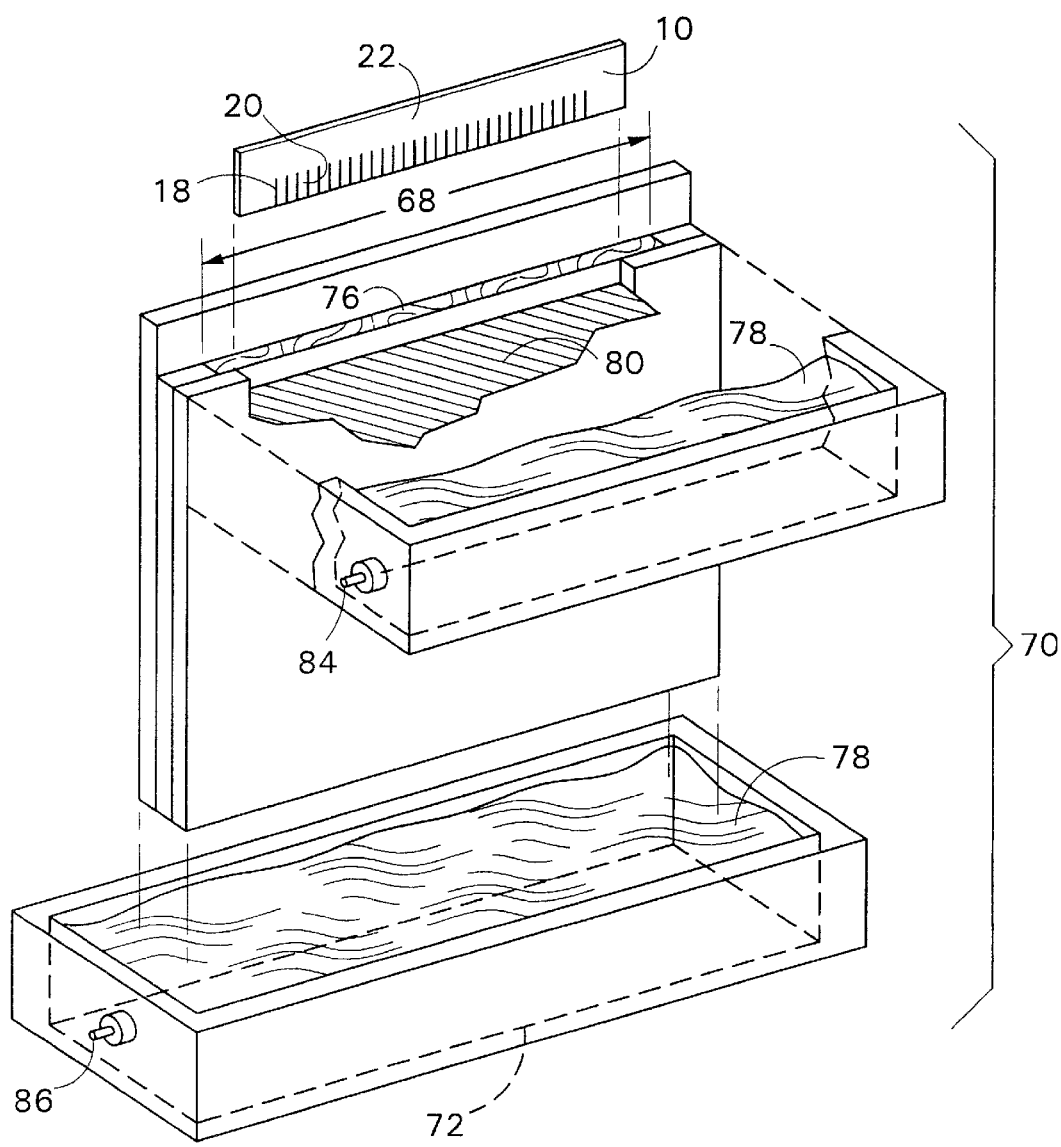
FIG. 10 is a perspective view of a vertical electrophoretic gel apparatus with a sample loading device according to the present invention; analyzed by polyacrylamide gel electrophoresis from a sample loading device of the present invention and of a sample loading device of the prior art method of using membrane scoring and the addition of hydrophobic ink.

The sample loading device 10 can then be inserted into a loading area 68 of a polyacrylamide gel electrophoresis apparatus 70 such as seen in perspective view in FIG. 10. The apparatus 70 has a well 72 in which a gel 74 is formed or placed. In order to facilitate the loading process, a liquid 76 with a higher viscosity than the buffer solution, such as "Ficoll" can be loaded into the well 72 to a level 78 which just exceeds an upper surface 80 of the gel 74 to further assist in preventing sample diffusion. After the apparatus 70 is filled with the viscous liquid 76, the sample loading device 10 is positioned within the apparatus 70 so that the sample loading areas 20 are positioned in proximity to the loading area, the top edge, 68 of the gel 74.

The polyacrylamide gel electrophoresis process can be initiated by placing a voltage across the gel via a cathode wire 84 and an anode wire 86 and establishing an electrophoretic field. This process, as described above, forces the samples by their charge to migrate from the sample loading device to the gel. After about five minutes, or when the samples are in the gel, the process can be halted and the sample loading device can be removed. The remaining PEG or glycerol can be washed out of the loading well by flushing with a pipette. The electrophoretic field can then be restarted and the polyacrylamide gel electrophoresis can be allowed to complete its full duration.

It is recognized in a preferred embodiment, the sample loading device 10 can have alignment indicators to assist in placing the sample loading device 10 in relation to the polyacrylamide gel electrophoresis apparatus 70.

The device 10 can also have lane marking aids to assist a user in locating particular sample loading lanes 20 in the manually spotting of samples on the device 11. A stiffening frame can also be utilized if the device 10 is to be handled robotically.

EXAMPLES

The following examples are for purposes of illustration only, and are not intended to limit the scope of the specification or appended claims.

For comparative analysis, a sample loading device according the prior art having both scoring and hydrophobic ink was prepared. Briefly, notches were scored into an absorbent membrane and then were filled with hydrophobic ink. The notches were scored with a push pin, and the hydrophobic ink was applied with a common Bic Round Stic ballpoint pen. The absorbent membrane was supportive nylon. Scoring involves removing absorbent membrane material from the substrate.

A sample loading device of the present invention was prepared using the rotary method, as shown in FIG. 4, to convert the absorbent membrane 14 into a sample diffusion barrier. A pressure of about 2500 psi was applied to the absorbent membrane to form the diffusion barriers.

To provide an accurate basis for comparison, the sizes and spacings of the prior art sample loading device (comparative comb) and the inventive sample loading device were the same as those discussed above with respect to FIG. 9B.

After preparation as described above, the comparative comb and the sample loading device of the present invention were used in an identical polyacrylamide gel electrophoresis system for comparison.

Three 96-well plates of double-stranded DNA templates, for a total of 288 samples, were prepared following the procedure described by Engelstein et al., "Template Preparation for High Throughput Sequencing," *Microbial and Comparative Genomics*, 3(4) (1988), and were sequenced using the Perkin Elmer (PE) Applied Biosystems standard Big *Dye Terminator Cycle Sequencing Ready Reaction Kit*, part #4303154, following the 1/4X BigDye Terminator Hydra Sequencing Reactions Protocol. Briefly, a reaction mix was prepared for per 100 reactions that includes 333.33 µl of BigDye mix, 167, µl of BigDye buffer, 447 µl of distilled water and 53 µl of (10 µM) primer. 10 µl of the reaction mixture was then added to a 0.2 ml Micro tube (March Biomedical Products, Rochester, N.Y.). 4 µl of DNA template (50 ng/µl) was then added to each tube. The tubes were then thermocycled following the manufacturer's instructions.

The same DNA template samples were used for the comparative comb and the sample loading device of the present invention.

Sequenced samples were precipitated and resuspended, except that the volume of resuspension was 1 µl rather than the standard 2 µl . Briefly, 40 µl of 75% ethanol was added to each sequencing reaction and then centrifuged for 30 minutes at 3000 rpm at 4° C. The plate was then inverted to remove the supernatant, followed by incubation at room temperature to allow the remaining fluid to evaporate.

0.5 µl of sample was then manually spotted, using a Rainin pipette, onto each of the comparative comb and the sample loading device of the present invention, where each contained 96 samples.

The comparative comb and the sample loading device of the present invention were then inserted into a 0.4 mm well, 0.2 mm 48 cm PE Applied Biosystems gel cassette. Data were collected on an ABI 377 automated sequencer for 10 hours at 2.8 kV. The raw data were transferred to ABI collection software for lane tracking. and initial analysis, and then to Phred for base calling and accuracy assessment. The results obtained from Phred were compared using JMP statistical analysis software.

More specifically, the raw data were analyzed by Phred software (Ewing et al., "Base-Calling of Automated Sequencer Traces Using Phred, 1. Accuracy Assessment," *Genome Research*, 8:175–185; and Ewing et al., "Base-Calling of Automated Sequencer Traces Using Phred, 11. Error Probabilities," *Genome Research*, 8:186–194). The results of the Phred analysis were compared using JMP statistical analysis software (JMP 3.2.2 SAS Institute Inc., SAS Campus Drive, Cary, N.C. 27513).

Figure 11:
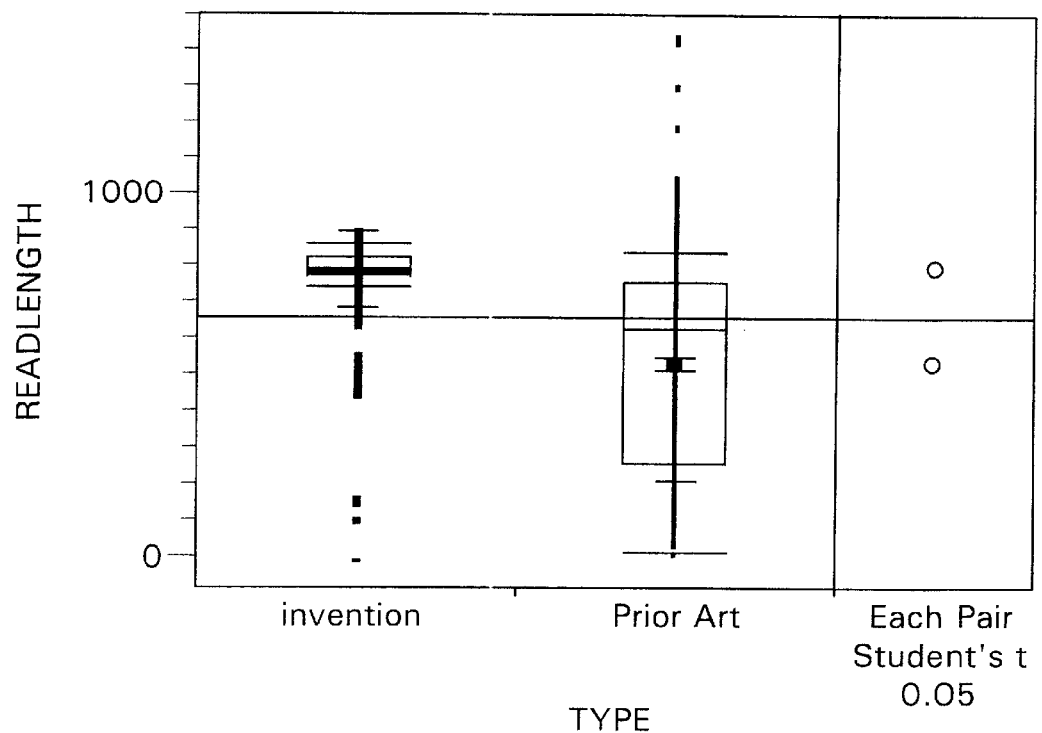

From the 288 samples, the comparative comb produced an average readlength/sample of 518 bases/sample with a standard deviation of 313 bases. From the 288 samples, the sample loading device of the present invention produced an average readlength/ sample of 785 bases/sample with a standard deviation of 108 bases. A student's t test at 95% confidence limits was performed comparing the data. The results of the student's t test indicated that each data set was significantly different from the other. The results are presented in FIG. 11 and in Table 1 below.

TABLE 1

| Sample | Number of Samples | Average Readlength in Bases | Standard Deviation | Standard Error Mean |
|---|---|---|---|---|
| comparative | 288 | 518.462 | 313.189 | 18.455 |
| inventive | 288 | 784.767 | 108.251 | 6.379 |

Phred analysis gives a measure of quality for each of the bases within a sequence call (Ewing et al., "Base-Calling of Automated Sequencer Traces Using Phred, 1. Accuracy Assessment," *Genome Research*, 8:175–185; Ewing et al., "Base-Calling of Automated Sequencer Traces Using Phred, H. Error Probabilities," *Genome Research*, 8:186–194). Phred assigns a number to each nucleotide it calls based on its confidence that the call is correct. The numbers are on a log scale and can range from 0 up. A call of 20 corresponds to a 99% probability that the base call is correct, while a call of 30 corresponds to a 99.9% probability that the base call is correct, while a call of 40 corresponds to a 99.99% probability that the base call is correct, and so on.

Figure 12:
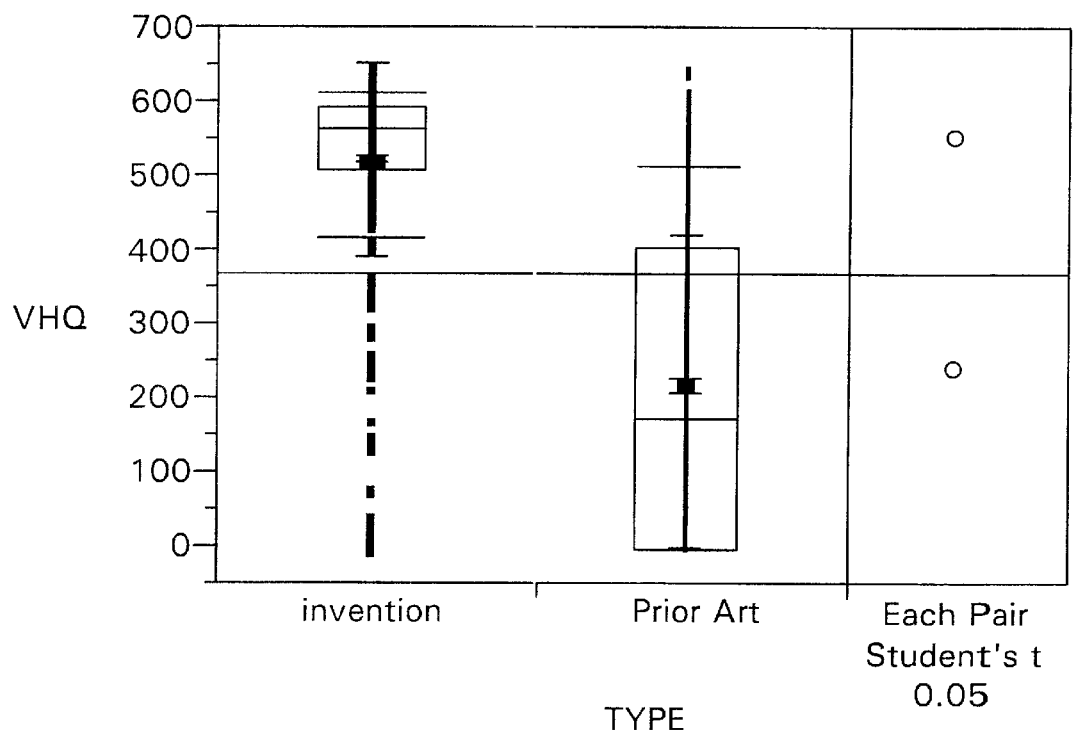
FIG. 12 is a graph comparing the Very High Quality/ sample of DNA sequences analyzed by gel electrophoresis from a sample loading device of the present invention and of a sample loading device of the prior art method of using membrane scoring and the addition of hydrophobic ink, as analyzed by Phred software.

A term is assigned (i.e., VHQ or Very High Quality data) to base positions with Phred scores greater than or equal to 30 (i.e., 99.9% confidence). The number of VHQ bases is compiled for each read. Looking at the number of VHQ bases achieved for the comparative comb and the sample loading device of the present invention, it can be seen that the sample loading device of the present invention had an average VHQ/sample of 522 bases with a standard deviation of 128 bases. The comparative comb had an average VHQ/sample of 212 bases with a standard deviation of 202 bases. A student's t test at 95% confidence limits was performed comparing the data. The results of the student's t test indicated that each data set was significantly different from the other. The results are presented in FIG. 12 and in Table 2 below.

TABLE 2

| Sample | Number of Samples | VHQ Bases | Standard Deviation | Standard Error Mean |
|---|---|---|---|---|
| comparative | 288 | 212.403 | 202.553 | 11.936 |
| inventive | 288 | 521.583 | 128.669 | 7.582 |

Based on the above results it can be seen that the sample loading device of the present invention achieved readlengths of 267 more bases than the comparative comb. These data show that the sample loading device of the present invention had a 51% increase in readlength over the comparative comb. Also, the sample loading device of the present invention achieved 310 more VHQ bases than the comparative comb. These data show that the sample loading device of the present invention had an increase of over 146% in the accuracy of the bases called. It is clear from these data that the sample loading device of the present invention produced results that were unexpectedly superior to the results produced by the comparative comb.

Each of the patent applications and publications cited in the present specification is hereby incorporated by reference herein in its entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. An electrophoresis gel sample loading device comprising:
    a laminate having backing material and
    an absorbent material carried by the backing material, the absorbent material being compressed in a plurality of regions to define diffusion barriers which are unable to absorb samples placed on the sample loading device.

2. The sample loading device of claim 1 wherein the backing material has an adhesive layer for securing the absorbent material to the backing material.

3. The sample loading device of claim 1 wherein the backing material is polymer tape.

4. The sample loading device of claim 3 wherein the backing material is a polyamide film tape.

5. The sample loading device of claim 3 wherein the backing material is a polyester film tape.

6. The sample loading device of claim 1 wherein the absorbent material is an unsupported, neutrally-charged nylon absorbent material.

7. The sample loading device of claim 6 wherein the absorbent material has a pore size in a range of 0.12 μm and 0.50 μm and the diffusion barrier of the absorbent material has a pore size reduced by greater than 89 percent of the sample loading area.

8. An electrophoresis gel sample loading device comprising:
    a laminate having a substrate and a homogenous absorbent material having a plurality of sample loading areas and a sample diffusion barrier interposed between adjacent sample loading areas, the diffusion barriers being materially altered homogenous absorbent material incapable of absorbing samples placed on the sample loading areas.

9. The sample loading device of claim 8 wherein the sample loading area of the absorbent material has a pore size in a range of 0.12 μm and 0.50 μm and the diffusion barrier of the absorbent material has a pore size less than 0.12 μm.

10. The sample loading device of claim 9 wherein the absorbent material is an unsupported, neutrally-charged nylon absorbent material.

11. The sample loading device of claim 10 wherein the backing material is a polyester film tape.

12. A method of making a sample electrophoresis gel loading device comprising the steps of:
    forming a laminate by providing a backing material;
    securing an absorbent material to the backing material;
    physically altering the absorbent material to reduce the percentage of open area in a plurality of regions to define sample diffusion barriers which are unable to absorb samples placed on the absorbent material.

13. The method of claim 12 wherein the step of physically altering the absorbent material is done by physically compressing the absorbent material.

14. The method of claim 12 wherein the step of physically altering the absorbent material is done by a combination of heat and pressure.

15. The method of claim 12 wherein the step of physically altering the absorbent material includes heating the absorbent material to reduce the percentage of open area to define the sample diffusion barriers.

16. The method of claim 12 wherein the absorbent material is physically altered to form the sample diffusion barriers by compressing the absorbent material between a rotating roller having a plurality of teeth for engaging the absorbent material and a platen.

17. The method of claim 12 wherein the absorbent material is physically altered to form the sample diffusion barriers by compressing the absorbent material between a stamping device having at least one projection moving translationally into engagement with the absorbent material.

18. The method of claim 12 wherein an adhesive is used to secure the absorbent material to the backing material.

19. The method of claim 12 further comprising the steps of:
    adding alignment indicators;
    adding lane markings; and
    adding a stiffening frame.

20. A method of loading samples into a gel of an electrophoresis gel system comprising the steps of:
    providing a sample loading device having an absorbent material with a plurality of sample loading areas and sample diffusion barriers of physically altered homogenous absorbent material;
    applying a sample to the sample loading device;
    placing the sample loading device in contact with a gel in a gel electrophoresis apparatus; and
    applying a voltage across the gel.

21. The method of loading samples into a gel of claim 20 further comprising the step of placing a viscous liquid in the electrophoresis apparatus to cover the gel.

22. An electrophoresis gel sample loading device comprising:
    a laminate having a substrate and an absorbent membrane affixed to the substrate; and a plurality of diffusion barriers formed from the absorbent membrane wherein the diffusion barriers are unable to absorb samples placed on the sample loading device.

23. The sample loading device of claim 22 wherein the substrate comprises a polyamide file tape.

24. The sample loading device of claim 22 wherein the substrate comprises a polyester film tape.

25. The sample loading device of claim 22 wherein the absorbent membrane comprises a neutrally-charged nylon material.

26. An electrophoresis gel sample loading device comprising:
   a laminate having a backing material; and
   an absorbent material carried by the backing material, the absorbent material altered in a plurality of regions to define diffusion barriers where the material is dramatically less absorbent and unable to absorb samples placed on the sample loading device.

27. The sample loading device of claim 26 wherein the backing material has an inert pressure sensitive adhesive layer for securing the absorbent material to the backing material.

28. The sample loading device of claim 27 wherein the adhesive backing a material is in a range of between 0.010 inches and 0.035 inches.

29. The sample loading device of claim 28 wherein the backing material is polymer film tape.

30. An electrophoresis gel sample loading device comprising:
   a laminate having a substrate and an absorbent membrane affixed to the substrate; and
   a plurality of heat-formed diffusion barriers formed from the absorbent membrane wherein the diffusion barriers are unable to absorb samples placed on the sample loading device.

31. The sample loading device of claim 30 wherein the substrate comprises a polyamide file tape.

32. The sample loading device of claim 30 wherein the substrate comprises a polyester film tape.

33. The sample loading device of claim 30 wherein the absorbent membrane comprises a neutrally-charged nylon material.

34. A method of making an electrophoresis gel sample loading device comprising the steps of:
   providing a substrate;
   providing an absorbent membrane;
   adhering the substrate and the absorbent membrane, forming a laminate;
   and
   forming a plurality of diffusion barriers on the absorbent membrane using a mechanical pressure.

35. The method of claim 34 further comprising the step of directing the laminate to a roller fabricated with a pattern of raised areas corresponding to a desired diffusion barrier profile.

36. The method of claim 34 further comprising the step of directing the laminate to a linear stamping device fabricated with a pattern of raised areas corresponding to a desired diffusion barrier profile.

37. A method of making an electrophoresis gel sample loading device comprising the steps of:
   providing a substrate;
   providing an absorbent membrane;
   adhering the substrate and the absorbent membrane, forming a laminate; and
   forming a plurality of diffusion barriers on the absorbent membrane using heat.

38. The method of claim 37 further comprising the step of directing the laminate to a roller fabricated with a pattern of heating filaments corresponding to a desired diffusion barrier profile.

39. The method of claim 37 further comprising the step of directing the laminate to a linear stamping device fabricated with a pattern of heating filaments corresponding to a desired diffusion barrier profile.

40. The method of claim 37 further comprising the step of providing heat using laser energy.

41. The method of claim 37 further comprising the step of providing heat using RF energy.

42. A sample loading device prepared by the process comprising:
   providing a laminate comprising an absorbent membrane affixed to a substrate, wherein the absorbent membrane is an unsupportive, neutrally-charged nylon, and wherein the substrate is Kapton™ tape or Mylar™ tape;
   applying some form of energy, such as heat, pressure, laser energy, RF energy or the like, to the laminate to form one or more sample diffusion barriers on the laminate.

* * * * *